(12) United States Patent
Andersen et al.

(10) Patent No.: US 8,684,983 B2
(45) Date of Patent: Apr. 1, 2014

(54) TO CONTROL BENDING IN A SKIN PLATE FOR USE IN AN OSTOMY APPLIANCE

(75) Inventors: Birthe Vestbo Andersen, Espergaerde (DK); Michael Hansen, Gilleleje (DK)

(73) Assignee: Coloplast A/S, Humlebaek (DK)

( * ) Notice: Subject to any disclaimer, the term of this patent is extended or adjusted under 35 U.S.C. 154(b) by 18 days.

(21) Appl. No.: 13/128,410

(22) PCT Filed: Nov. 12, 2009

(86) PCT No.: PCT/DK2009/050298
§ 371 (c)(1),
(2), (4) Date: May 10, 2011

(87) PCT Pub. No.: WO2010/054662
PCT Pub. Date: May 20, 2010

(65) Prior Publication Data
US 2011/0218507 A1      Sep. 8, 2011

(30) Foreign Application Priority Data
Nov. 12, 2008   (DK) .................................. 2008 01571

(51) Int. Cl.
*A61M 1/00*     (2006.01)
*A61F 5/44*     (2006.01)

(52) U.S. Cl.
USPC ........... 604/338; 604/317; 604/327; 604/332; 604/337; 604/339; 604/341; 604/342; 604/343; 604/344; 604/345; 604/355

(58) Field of Classification Search
None
See application file for complete search history.

(56) References Cited

U.S. PATENT DOCUMENTS

| | | | |
|---|---|---|---|
| 2,675,001 A | 4/1954 | Jones | |
| 2,684,675 A | 7/1954 | Perry | |
| 2,928,393 A | 3/1960 | Marsan | |
| 4,219,023 A | 8/1980 | Galindo | |
| 4,723,952 A * | 2/1988 | Esposito | 604/338 |
| 5,163,930 A | 11/1992 | Blum | |
| 5,429,625 A * | 7/1995 | Holmberg | 604/338 |
| 5,607,413 A * | 3/1997 | Holmberg et al. | 604/342 |
| 5,618,276 A * | 4/1997 | Leise et al. | 604/336 |
| 6,569,134 B1 * | 5/2003 | Leise et al. | 604/332 |
| 2003/0088219 A1 * | 5/2003 | Metz et al. | 604/339 |

FOREIGN PATENT DOCUMENTS

| | | |
|---|---|---|
| EP | 0894482 | 2/1999 |
| EP | 1464308 | 10/2004 |

OTHER PUBLICATIONS

Main, K., et al. "Influence of sex and growth hormone deficiency on sweating," Scand J Clin Lab Invest; 51: pp. 475-480, 1991.
Chinese office action dated Nov. 26, 2013 from Chinese Patent Application No. 200980144791.2 attached.

* cited by examiner

*Primary Examiner* — Oren Ginsberg
*Assistant Examiner* — Joshua Lee
(74) *Attorney, Agent, or Firm* — Coloplast Corp., Coloplast A/S; Nick Baumann

(57) ABSTRACT

A convex shell for use in a base plate of an ostomy appliance includes an annular ring defined by an outer edge and an inner edge of defining a through-going hole. The annular ring has at least four transition sections extending transversely across the annular ring, dividing the annular ring into at least a first, second, third and fourth segment. By changing the characteristics of the convex shell in such sections, it is possible to control the bending of the shell. The shell also makes it possible to keep the area around the stoma more stable and resistant towards collapsing, while providing improved flexibility in the peristomal area for better comfort.

20 Claims, 4 Drawing Sheets

TO CONTROL BENDING IN A SKIN PLATE FOR USE IN AN OSTOMY APPLIANCE

CROSS-REFERENCE TO RELATED APPLICATIONS

This application is a nationalization of PCT/DK2009/050298 filed Nov. 12, 2009.

BACKGROUND OF THE INVENTION

1. Field of Invention

The invention relates to a skin plate for use in an ostomy appliance, wherein the bending of the skin plate occurs at desired areas. In particular, a convex shell is described for use in a skin plate wherein bending is focused to at least four sections.

2. Description of the Prior Art

Skin plates, also called base plates, are used in ostomy appliances to attach ostomy bags to the skin of a user having a stoma, the user also being referred to as an ostomate.

The skin plate is typically formed by a backing layer, e.g. a polyurethane film, on which a skin friendly adhesive is disposed. A through-going hole is arranged in the skin plate to receive a stoma so that the skin plate may be adhered to the skin surrounding the stoma.

In order to collect output from the stoma, the opening of an ostomy bag is arranged around the through-going hole. The ostomy bag may for example be arranged by welding the bag to the backing layer of the skin plate. This is in the art referred to as a one-piece ostomy appliance. Alternatively, a coupling arrangement, either adhesively or mechanically may be arranged so that ostomy bags may be arranged detachably on the skin plate. This allows the bag to be changed when full without detaching the skin plate from the skin. In the art, this is referred to as a two-piece ostomy appliance.

A number of ostomates develop so-called sunken/retracted stomas. This is where a stoma sinks into the abdomen which creates a recess in the stomach where the stoma is placed. Applying a planar skin plate around such a stoma would for one thing leave the area around the stoma uncovered and thereby, exposed to the output from the stoma. Moreover, in some cases the stoma is retracted so much that it is not even possible for it to extend through the through-going hole in the skin plate. In order to address the issue of sunken stoma convex skin plates has been developed.

These have a convex surface contour where an outer planar area is adhered to an outer skin area which surrounds the stoma, but where the skin is not pulled inwards towards the stoma. An intermediate area of the convex surface, having a slanting surface along the axis of the through-going hole, adheres to the skin area between the outer skin area and the inner skin area described hereafter. Finally, an inner planar area of the convex surface is adhered to an inner skin area which immediately surrounds the stoma.

Typically and described in general, such convex skin plates are manufactured by forming a planar skin plate as described above to a convex shell. The convex shell has the desired contour and shape and is formed in a material which is more rigid than the planar skin plate. The planar skin plate is pressed to the shape of the convex shell thereafter they are joined together, typically by welding or adhesive.

Thus, by choosing a suitable shell having a contour and shape which fit the characteristics of the sunken stoma, an ostomy appliance may be provided which snugly fits around the stoma, reducing the risk that output from the stoma gets in contact with the surrounding skin.

It has shown that the tissue surrounding such sunken stoma in some cases, in particular when relating to overweight and obese people, collapses around the convex skin plate. During such collapse, there is a risk the skin plate is dislodged or that the skin plate folds across the stoma and closes off the function of the stoma.

Furthermore, during activity the movement of the body causes constant bending around with the risk of creating pressure ulcers.

As will be described herein, it has been shown that by controlling where and how the skin plate bends it is possible to improve the stability of the area around the stoma and to distribute the load on the convex skin plate so that the risk of dislodging and pressure ulcers is reduced.

SUMMARY OF THE INVENTION

In a first aspect, the invention relates to a convex shell for use in a base plate of an ostomy appliance, the convex shell comprising an annular ring defined by an outer edge and an inner edge defining a through-going hole, said ring having a higher flexibility around a first axis which is perpendicular to the centre axis of the through-going hole relative to the flexibility around a second axis having an angle to the first axis and being perpendicular to the centre axis of the through-going hole.

By providing a convex shell having a varied flexibility, it is possible to control how the base plate of an ostomy appliance folds during use, resulting in improved comfort for the user and decreasing the risk of the ostomy appliance detaching from the skin.

In one embodiment, the convex shell comprises an outer planar surface extending in a first plane perpendicular to the centre axis C-C of the through-going hole, the outer planar surface extending radially inwards from the outer edge and transitioning into an intermediate slanting surface, where the intermediate slanting surface extends radially inwards from the outer planar surface towards an inner planar surface, where the inner planar surface extends in a second plane perpendicular to the centre axis C-C of the through-going hole and extends radially from the intermediate slanting surface towards the inner edge defining the through-going hole.

In another embodiment of the convex shell, a first angle is defined between the slanting surface and the inner planar surface along the first axis, a second angle is defined between the slanting surface and the inner planar surface along the second axis; and the first and second angle are different.

In particular, the first angle can be between 40° and 60°, in particular 50°, and the second angle can be between 25° and 45°, in particular 35°. Advantageously, the first angle gradually decreases towards the second angle.

This allows for a convex shell having varying flexibility and making it possible to determine how sharp the bend can be. For example, a very steep change in the angle creates a bend in a very small area, while a change over a large area creates a smother bend. This is, for example, useful in reducing the risk of pressure wounds.

Alternatively or additionally, the bend can be controlled by providing a convex shell, wherein a first thickness of the convex shell along the intermediate slanting surface along the first axis is different from a second thickness of the convex shell along the intermediate slanting surface along the second axis. The first thickness can, for example, gradually taper towards the second thickness.

In a second aspect, either in combination with the first aspect above or separately, the present invention relates to a convex shell for use in a base plate of an ostomy appliance, the convex shell comprises an annular ring defined by an outer edge and an inner edge defining a through-going hole, said ring further comprising at least four transition sections extending transversely across the annular ring, dividing the annular ring into at least a first, second, third and fourth segment.

From the term it should be understood that a 'transition section' is a section wherein the characteristics between two neighbouring segments of the convex shell changes.

By changing the characteristics of the convex shell in such sections, it is possible to control the bending of the shell and, as will be described herein, it will be possible to keep the area around the stoma more stable and resistant towards collapsing, while providing improved flexibility in the peristomal area for better comfort.

Furthermore, as described above, a convex shell is an element used for manufacturing of convex skin plates. The convex shell is characterised in that it has a convex surface contour. An outer planar surface is provided annularly along the outer edge, and extends mainly in one plane. The outer planar surface extends radially inwards towards where it continues into an intermediate slanting surface, which both extends radially inwards but also extends along the axis of the through-going hole. Finally the intermediate slanting surface transitions into an inner planar surface which is provided annularly along the inner edge and extends mainly in another plane than the one the outer planar surface extends in.

As may be understood, in other words, the outer planar surface is axially displaced along the axis of the through-going hole in respect to the inner planar surface. The radius from the axis of the through-going hole to the outer edge of the inner planar surface is smaller than the radius from the axis of the through-going hole to the inner edge of the outer planar surface, and the inner planar surface is connected to the outer planar surface by an intermediate slanting surface.

In one embodiment, the annular ring has an oval shaped outer edge and/or the inner edge is shaped as an oval. This provides a convex shell which has a shape which follows the curvature of folds and movement of the body and thus is more comfortable to wear.

Such an oval shape is typically symmetrical around a first and a second axes and in that the at least four transition sections are arranged closest to the axis of which the oval shape has the largest extent. However, other symmetrical configuration may be used, e.g. the oval is only symmetrical around one axis and/or the transition sections are closer to the axis with the smallest extent of the oval shape.

In one embodiment, the transition sections are provided as grooves. This is a simple and easy way to control bending in an object. Bending will usually occur in areas having less amount of material opposed to areas having a higher amount of material as this result in a higher rigidity of the object in these areas.

In one embodiment, the segments are arranged symmetrically. This can for example be done by arranging the first and third segments opposite each other, and the second and fourth segments opposite each other.

In another embodiment, the first and third segments have a higher thickness than the second and fourth segments. This is an additional and/or alternative way to control the bending. This would result in that the shell will tend to bend in the transition sections where the thickness changes.

In another embodiment, the first and third segment is formed by a different material than the second and fourth segments, which is another and/or alternative way to control the bending.

In another embodiment, the second and fourth segments have a higher flexibility than the first and third segments.

In order to achieve increased stability around the stoma some users additionally prefer to wear a belt which is attached to the convex skin plate. Thus, in one embodiment a skin plate is provided comprising at least four belt attachment means. For example, at least four belt loops may be arranged along the outer edge of the annular ring.

For such embodiment, a belt will typically be provided which comprises at least four skin plate attachment means allowing the skin plate and the belt to be coupled together.

The convex shell may be joined to the skin plate in different ways. In one embodiment, the convex shell is attached to a backing layer whereon an adhesive suitable for adhering to the skin is applied.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
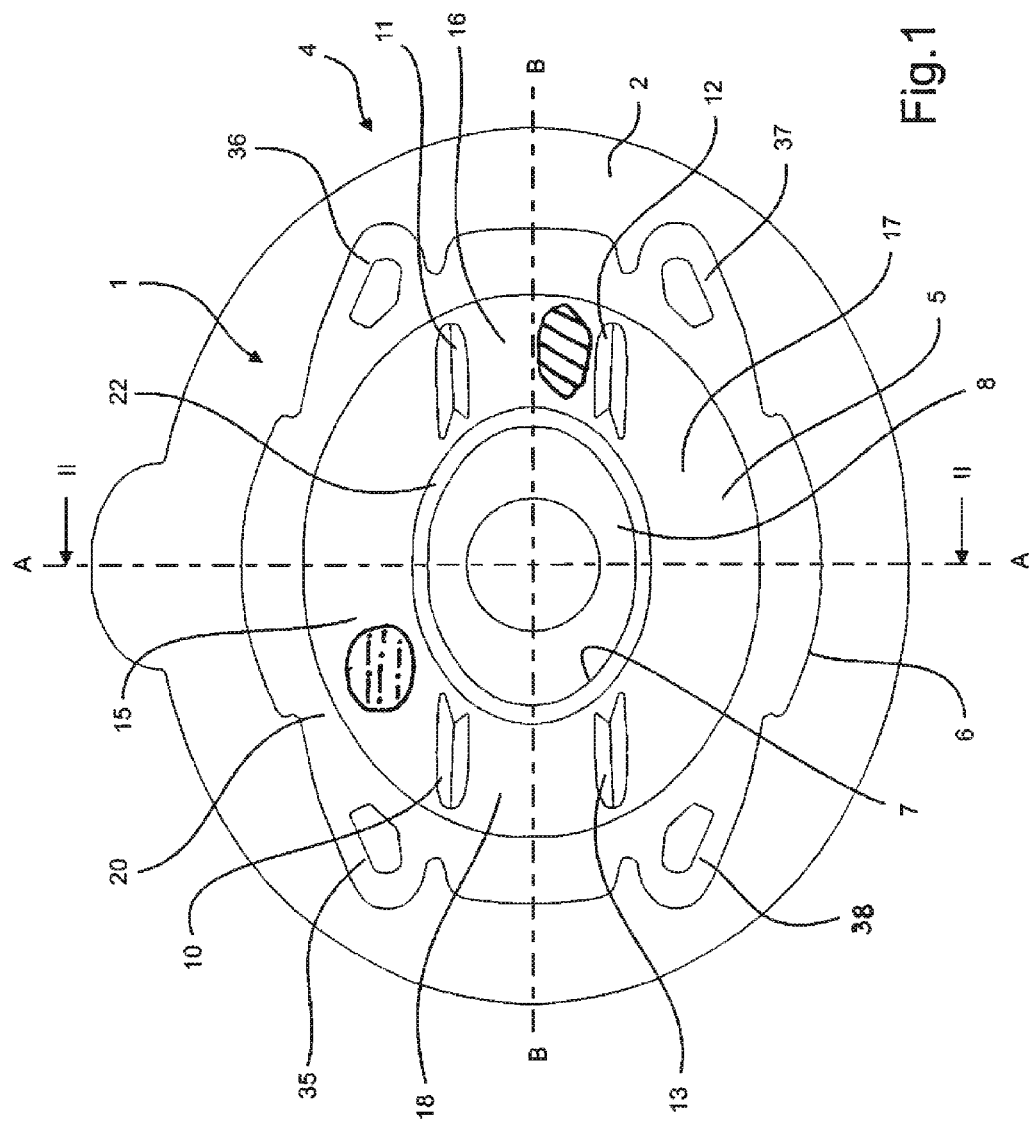
FIG. 1 shows a top view of a convex shell.
Figure 2:
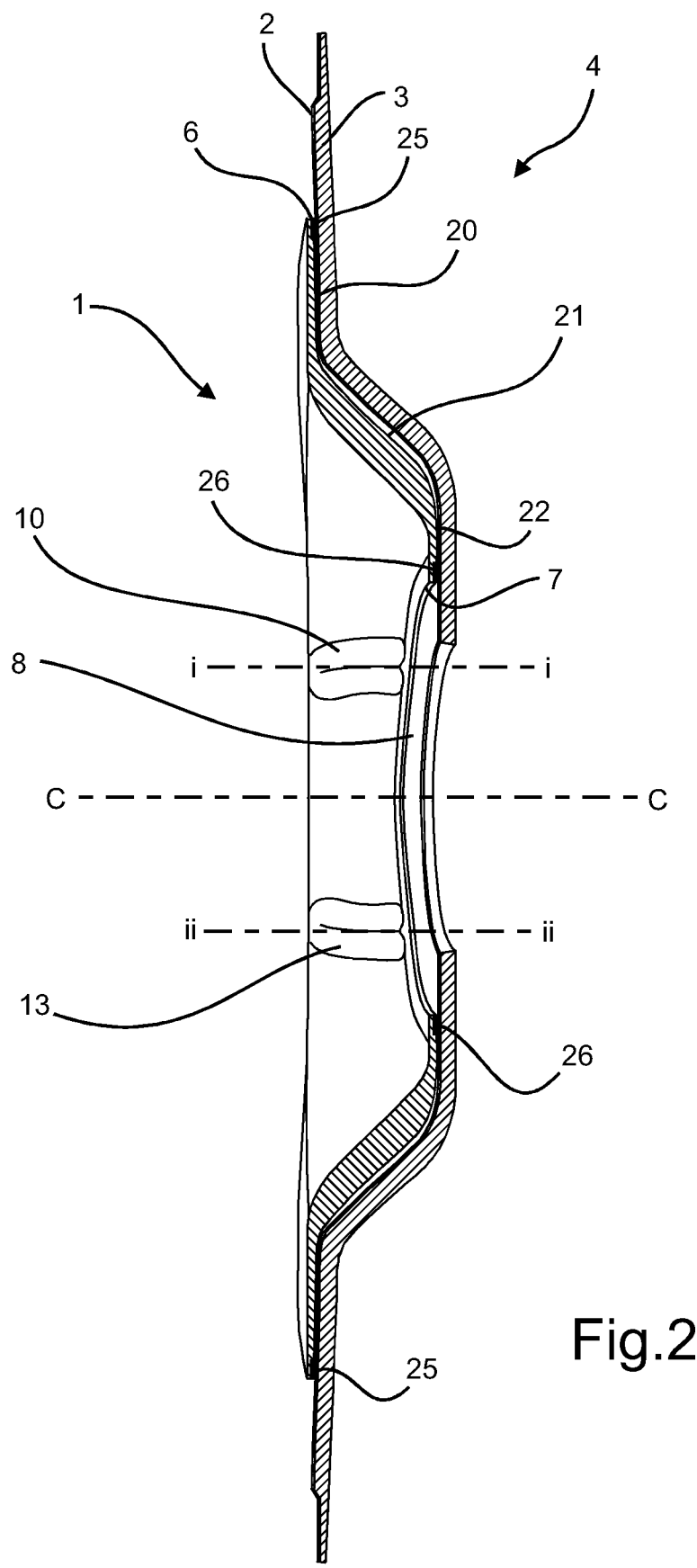
FIG. 2 shows a side view and in section of the convex shell of FIG. 1 along line II-II.

One embodiment of a convex shell 1 is shown in FIGS. 1 and 2. The convex shell is attached to backing layer 2 whereon a skin friendly adhesive 3 is applied. Together the convex shell, backing layer and adhesive form a convex skin plate 4.

The convex skin plate is part of an ostomy appliance (not shown), for example by welding an ostomy pouch (not shown) to the backing layer or the convex shell or using coupling means (not shown) which allows the ostomy pouch to be detachably attached to the convex skin plate.

The convex shell 1 comprises an annular ring 5 defined by an outer edge 6 and an inner edge 7. The inner edge 7 defines a through-going hole 8 which has an axis C-C. Furthermore, when considering the convex shell along the axis C-C of the through-going hole 8, the convex shell is symmetrical around axes A-A and B-B, which are perpendicular to each other.

In use the convex shell will preferably be applied on a user so the axis A-A will be mainly vertical and the axis B-B will be mainly horizontal when a user is standing. Or, in other words, the convex shell will be applied so that the natural movements of the user will cause the convex shell, and thereby the convex skin plate, to bend around the axis B-B.

Four transition sections, formed as first, second, third and fourth grooves 10,11,12,13 extend transversely across the annular ring. The grooves divide the annular ring into at least a first segment 15 defined by the first and second grooves; a second segment 16 defined by the second and third grooves;

a third segment 17 defined by the third and fourth grooves; and a fourth segment 18 defined by the fourth and first grooves.

The grooves do not necessarily extend all the way across the annular ring, which also is the case of the embodiment of FIGS. 1 and 2. The desired effect as will be described later may also be provided by only partially extending grooves.

As can be seen in particular from FIG. 2, the convex shell has a convex surface contour. It should be understood that the term convex shell should be interpreted broadly as the shape does not have to be the mathematically correct representation of convex, but may be e.g. trapezoidal or circular.

For example, a convex shell can in broader terms be understood as being a shell having an outer planar surface 20 which is provided annularly along the outer edge 6 of the annular ring, and extends mainly in one plane. The outer planar surface 20 extends radially inwards, in respect to the axis C-C of the through-going hole 8, until it transitions into an intermediate slanting surface 21, which both extends radially inwards but also extends along the axis C-C of the through-going hole 8. Finally the intermediate slanting surface 21 transitions into an inner planar surface 22 which is provided annularly along the inner edge 7 and extends mainly in another plane than the one the outer planar surface 20 extends in.

As may be understood, in other words, the outer planar surface 20 is axially displaced along the axis C-C of the through-going hole 8 in respect of the inner planar surface 22. The maximum radial extent of the inner planar surface 22 is smaller than the minimum radial extent of the outer planar surface 20, and the inner planar surface 22 is connected to the outer planar surface 20 by the intermediate slanting surface 21.

It will mainly be the intermediate slanting surface 21, which decides the contour of the shell.

The convex shell 1 is attached to the backing layer 2 by a first annular weld 25 between the outer planar surface 20 and the backing layer 2, and a second annular weld 26 between the inner planar surface 22 and the backing layer 2. It should be understood that the means and place of attachment are not relevant to the present invention and other means could be used, e.g. an adhesive or a soluble, and it could be attached to other places for example at the intermediate slanting surface 21 and the attachments may be interrupted.

A hole 27 is provided in the backing layer 2 and adhesive 3 which is coaxially aligned with the through-going hole 8 of the convex shell.

As can be seen in FIG. 2, the first groove 10 extends along an axis i-i and the fourth groove 13 extends along an axis ii-ii. In a similar way, although not shown, the second groove 11 extends along the axis i-i, and the third groove 12 extends along the axis ii-ii.

Figure 3:
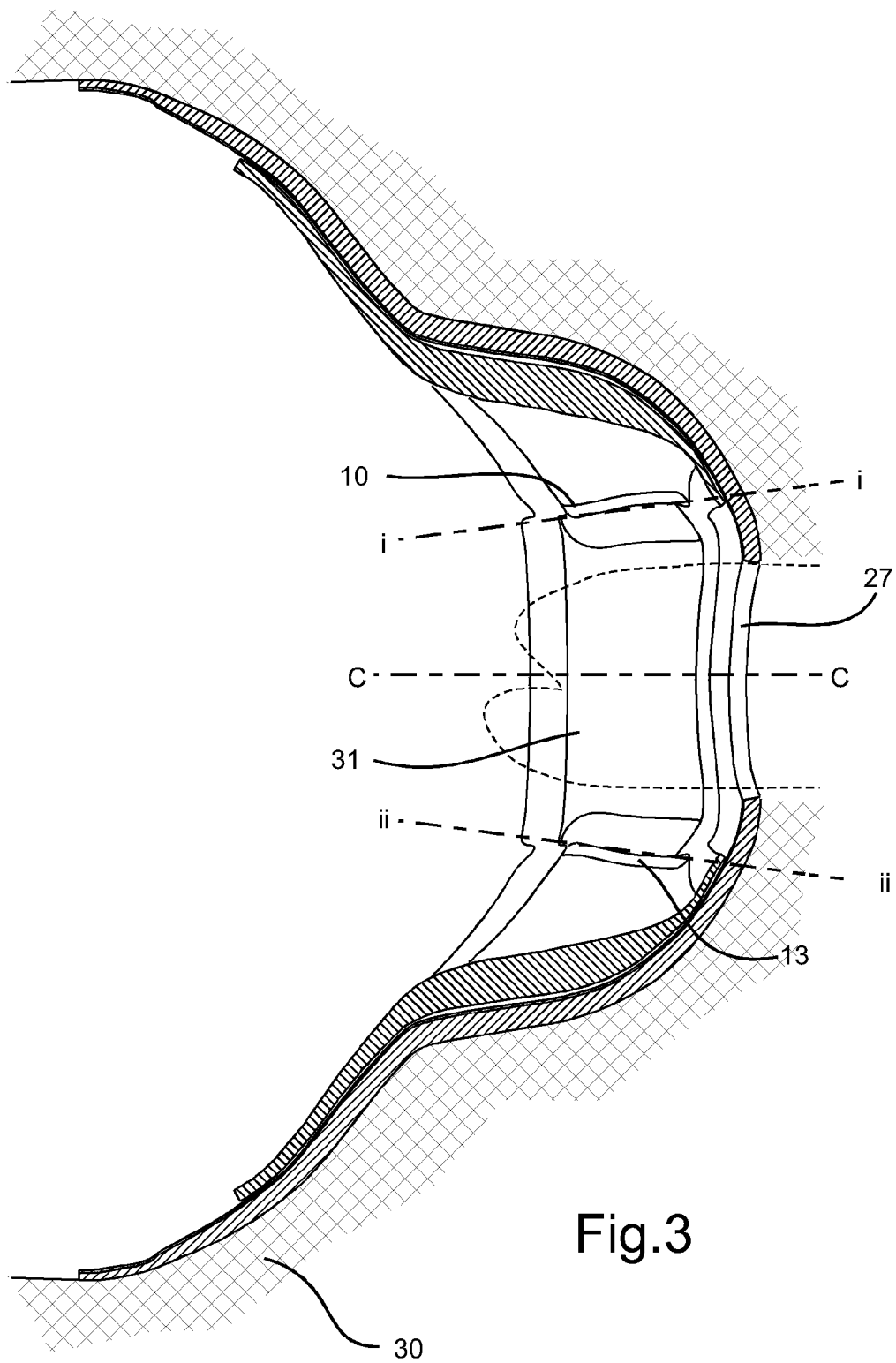
FIG. 3 shows a side view along same intersection as in FIG. 2 of a convex shell during use.

When applied to a user, as shown in FIG. 3, the adhesive side is attached to the skin 30 so that a stoma 31 (which for illustrative purposes is shown with interrupted lines) is received through the hole 27 and the through-going hole 8. Before applying the user might need to manually cut the hole 27 into a shape corresponding to his/hers stoma in order for the convex skin plate to fit snugly around the stoma.

When the user is active as shown in FIG. 3, e.g. by bending, the motion will cause the convex skin plate to deform. In traditional skin plates, this will cause a deformation around a point lying along a deformation axis (not shown) parallel to the axis B-B, in a plane defined by the axis B-B and the axis C-C. However, due to the first and fourth grooves 10, 13 (and second and third grooves which are not shown) the deformation will mainly occur in the grooves, i.e. in points lying along the axes i-i and ii-ii. This reduces the deformation of the stoma considerably.

At the same time, since bending occurs around two axes (i-i and ii-ii) instead of one (C-C) the load, i.e. the forces applied to the convex skin plate by the user when active, is distributed over twice the area thereby reducing the risk of pressure wounds.

Thus, as may be understood, the reduced material in the transition sections provided by grooves results in a transfer of the major part of the deformation away from the stoma area and to an area capable of better absorbing the loads.

In order to follow the contour of the body, the grooves (transition sections) may additionally be arranged at an angle to the horizontal axis B-B. This allows the bend at the grooves to follow the curvature of the abdomen and any skin folds which may occur.

It is the change of characteristics of the convex shell in these transition sections which allows for controlling the bending, and the transition sections are not limited to be provided as grooves in order to obtain this function.

Alternatively the transition sections may be provided by a change in material used to manufacture the convex shell. Thus, using the embodiment of FIG. 1-FIG. 3, second segment 16 and the fourth segment 18 may be formed of a material which is more rigid than a second material used to provide the first segment 15 and the third segment 17. The relative more rigid second and fourth segment 16,18 will keep the stoma and the area surrounding it more stable during activity, while transferring the major part of the deformation to the transition sections and the first and third segment 15,17. Such rigidity may alternatively/additionally be provided by a different thickness in the material of the corresponding segment, making thicker segments more rigid and thus more stable toward deformation.

Moreover, the shape of the convex shell may also provide stability. Thus, for example, by shaping the through-going hole 8 as an oval, a higher stability is provided around the stoma and the area surrounding it.

It should be understood that although in some cases deformation may be undesirable it is mainly not a desire to remove deformation but mainly to control where deformation is occurring. A convex skin plate allowing for too little deformation, i.e. being too rigid, is uncomfortable to the user. Thus, it is a matter of compromise to obtain a product which is very flexible while still being rigid in some areas in order to provide both the convex shape but also to control where it is deformed.

Other ways of controlling the deformation and/or of preventing complete collapse (the first segment and the third segment fold onto each other) of the ostomy appliance and thereby risking that access to the ostomy pouch (not shown) is closed off, are achieved by four so-called belt ears 35, 36, 37, 38 provided along the outer edge of the convex shell. The belt ears function as a belt attachment means for attaching a belt (not shown) to the convex skin plate. The belt further reduces the risk that the skin plate dislodges from the skin.

By providing the belt ears at selected points along the outer edge of the convex shell, it is furthermore possible to control the deformation of the convex skin plate.

Similar to the transition section, it is thus prevented that deformation only occurs around a point lying along a deformation axis which crosses the stoma and thus deformation of the stoma, but rather that the majority of the deformation is transferred to areas away from the stoma by attaching the belt in places along two axes arranged along respective opposite sides outside of the area of the stoma.

By arranging the belt ears further from the horizontal axis B-B than the transition sections, it is prevented that force is applied within the area of the stoma and thus reducing the risk of deforming the stoma during use.

Figure 4:
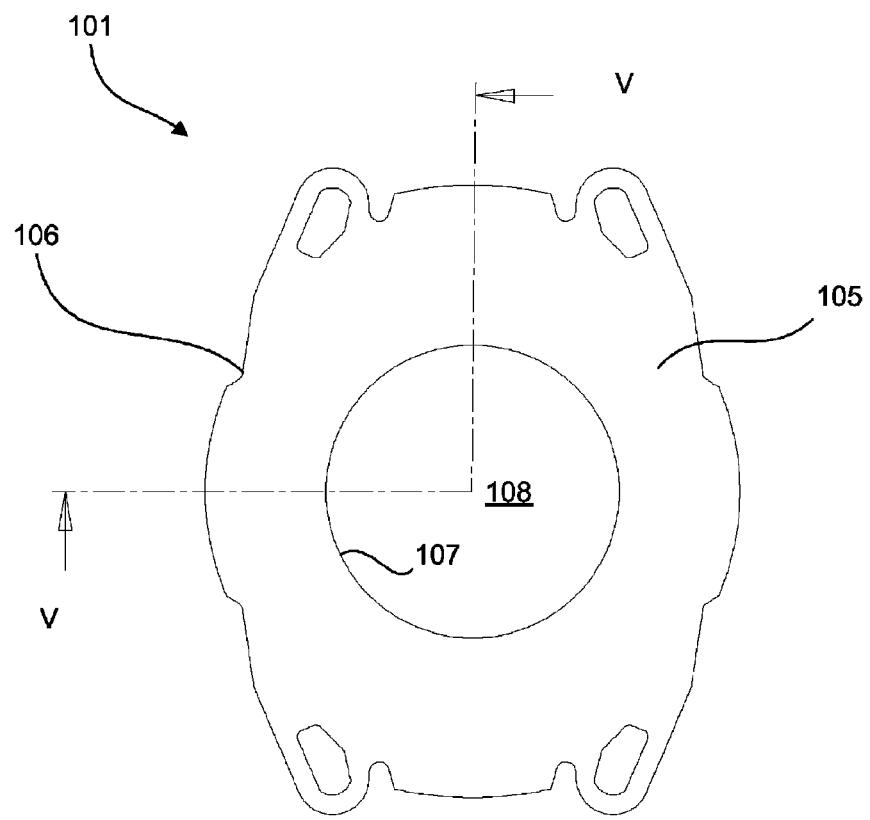
FIG. 4 shows a top view of a second embodiment of a convex shell.
Figure 5:
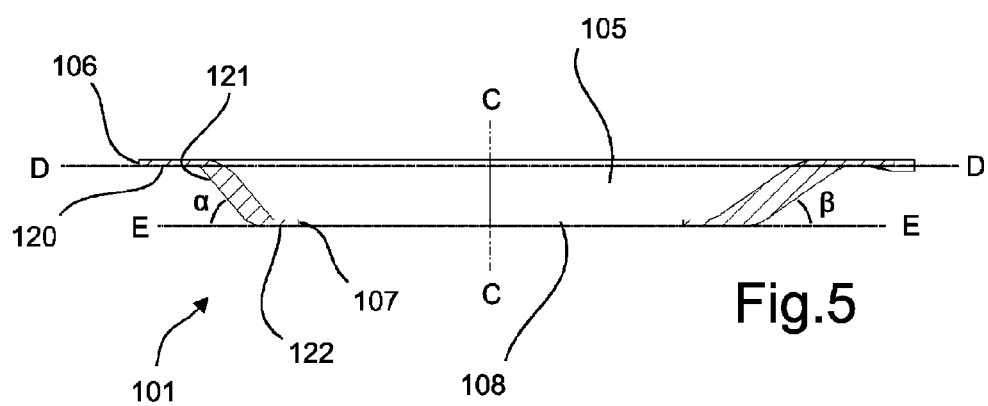
FIG. 5 shows a side view in section of the second embodiment of the convex shell of FIG. 4 along line V-V.

A second embodiment of the convex shell 101 is shown in FIG. 4 and FIG. 5. The convex shell is formed of an annular ring 105 defined by an outer edge 106 and an inner edge 107. The inner edge defines a through-going hole 108.

The convex shell has an outer planar surface 120, which extends in a first plane D-D. The first plane is perpendicular to the centre axis C-C of the through-going hole 108. The outer planar surface extends radially inwards from the outer edge and transitions into an intermediate slanting surface 121. The intermediate slanting surface 121 extends along the centre axis C-C and radially inwards from the outer planar surface and transitions into an inner planar surface 122. The inner planar surface extends in a second plane E-E perpendicular to the centre axis C-C of the through-going hole. The inner planar surface extends radially from the intermediate slanting surface towards the inner edge defining the through-going hole.

By changing the angle along the intermediate slanting surface so that it has different angles, a varied flexibility can be obtained, thereby allowing to control the bending of the base plate and solving the problems as previous discussed.

As shown in FIG. 5, the angle of the intermediate slanting surface can be set as being the angle between the surface and the second plane E-E. Thus, in one area it forms the angle α and in another are it form the angle β. If the angle α is set to 50° and the angle β is set to 35°, the convex shell will have a higher stiffness when trying to bend it around the area with the angle α compared to trying to bend it around the area with the angle β.

The change in the angle may be done in one step, however, a continuous transition provides a soft bending area which is gentle to the skin and reduces the risk of creating pressure wounds.

In addition to the different angles along the intermediate slanting surface, the convex ring is also provided with a varied thickness, $t_1$ and $t_2$ at the intermediate slanting surface which is another way of controlling the bending and flexibility of the convex ring.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

REFERENCE NUMBERS 1. convex shell
2. backing layer
3. skin friendly adhesive
4. convex skin plate
5. annular ring
6. outer edge
7. inner edge
8. through-going hole
9. first groove
10. second groove
11. third groove
12. fourth groove
15. first segment
16. second segment
17. third segment
18. fourth segment
20. outer planar surface
21. intermediate slanting surface
22. inner planar surface
25. first annular weld
26. second annular weld
27. hole
30. skin
31. stoma

What is claimed is:

1. A convex shell for use in a base plate of an ostomy appliance to be worn by an ostomate, the convex shell comprising:
    an annular ring with a convex shape contour on an inner surface facing the ostomate having an outer edge and an inner edge defining a through-going hole having a center axis, said ring having a longitudinal length and a lateral width, said ring having a first flexibility around a first axis that is perpendicular to the center axis of the through-going hole, said first axis extending substantially parallel with said longitudinal length, and a second flexibility around a second axis different than the first axis, said first flexibility being greater than said second flexibility, the second axis also being perpendicular to the center axis of the through-going hole,
    the annular ring including at least four transition sections defined by grooves that extend longitudinally across the annular ring, each groove extending from adjacent the inner edge of said through-going hole toward the outer edge of the ring to divide the annular ring into at least a first segment, a second segment, a third segment, and a fourth segment, said grooves configured to produce controlled bending of the shell along the grooves,
    wherein the convex shell includes an outer planar surface extending in a first plane perpendicular to the center axis of the through-going hole, the outer planar surface extending radially inwards from the outer edge and transitioning into an intermediate slanting surface, the intermediate slanting surface extending radially inwards from the outer planar surface towards an inner planar surface, and the inner planar surface extending in a second plane perpendicular to the center axis of the through-going hole and extending radially from the intermediate slanting surface towards the inner edge defining the through-going hole, said intermediate slanting surface forming said convex shape contour on the inner surface of the ring.

2. The convex shell according to claim 1, wherein
    a first angle is defined between the slanting surface and the inner planar surface along the first axis,
    a second angle is defined between the slanting surface and the inner planar surface along the second axis, and
    the first angle and the second angle are different.

3. The convex shell according to claim 2, wherein the first angle is between about 40° and 60°, and the second angle is between about 25° and 45°.

4. The convex shell according to claim 1, wherein a first thickness of the convex shell along the intermediate slanting surface along the first axis is different from a second thickness of the convex shell along the intermediate slanting surface along the second axis.

5. The convex shell according to claim 4, wherein the first thickness gradually tapers towards the second thickness.

6. The convex shell according to claim 1, wherein the outer edge of the annular ring is elliptical so that said longitudinal length is greater than said lateral width, and said inner edge is oval shaped, said elliptical and oval shaped edges being formed during manufacture.

7. The convex shell according to claim 6, wherein the second axis extends widthwise and is substantially perpendicular to said first axis and the elliptical outer edge is symmetrical around said first axis and said second axis, and wherein the first and third segments are positioned on opposing sides of the first axis and the second and fourth segments are positioned on opposing sides of the second axis, the at least four transition sections being arranged closer to the first axis that extends along the longitudinal length of the ring than to the second axis.

8. The convex shell according to claim 7, wherein the first segment and the third segment are symmetrical with one another and arranged opposite each other and the second segment and the fourth segment are symmetrical with one another and arranged opposite each other, said grooves extending substantially parallel with said first axis and spaced symmetrically on either side thereof.

9. The convex shell according to claim 8, wherein the first segment and the third segment are thicker than the second segment and the fourth segment.

10. The convex shell according to claim 8, wherein the first segment and the third segment have a different material of construction than the second segment and the fourth segment.

11. The convex shell according to claim 8, wherein the first segment and the third segment have a higher flexibility than the second segment and the fourth segment.

12. The convex shell according to claim 1, further comprising at least one belt loop provided on the outer edge of the annular ring.

13. The convex shell according to claim 1, wherein the convex shell is attached to a backing layer on which an adhesive suitable for adhering to skin is applied.

14. The convex shell as set forth in claim 1, wherein said grooves are formed on an outer concave surface of said shell opposite said convex inner surface, said convex inner surface being smooth.

15. A convex skin plate as part of an ostomy appliance to be worn by an ostomate, the convex skin plate comprising:
   a backing layer having a skin friendly adhesive thereon; and
   a convex shell attached to the backing layer, said convex shell including,
      an elliptical ring with a convex shape contour on an inner surface facing the ostomate, said ring as made having an elliptical outer edge and an elliptical inner edge defining a through-going hole having a center axis, said elliptical ring having a length defining a longitudinal axis that is perpendicular to the center axis and a width defining a lateral axis that is also perpendicular to the center axis, said length being greater than said width, said ring having a first flexibility around the longitudinal axis and a second flexibility around the lateral axis, said first flexibility being greater than said second flexibility; and
   the elliptical ring including at least four transition sections that extend longitudinally across at least part of the elliptical ring, each transition section extending from adjacent the inner edge of said through-going hole toward the outer edge of the ring to divide the elliptical ring into at least a first segment, a second segment, a third segment, and a fourth segment, said transition sections providing for controlled bending of the shell, wherein the transition sections in said convex shell are formed used to manufacture the shell so that some of the segments are more rigid than other of the segments.

16. The convex skin plate as set forth in claim 15, wherein said transition sections in said convex shell include grooves on a concave outer surface of said shell opposite said convex inner surface, said convex inner surface being smooth.

17. The convex skin plate according to claim 15, wherein the lateral axis is substantially perpendicular to said longitudinal axis and the outer edge of the elliptical ring is symmetrical around said longitudinal axis and around said lateral axis, the first and third segments being positioned on opposing sides of the longitudinal axis and the second and fourth segments are positioned on opposing sides of the lateral axis, the at least four transition sections being arranged closer to the longitudinal axis than to the lateral axis.

18. The convex skin plate according to claim 15, wherein the transition sections in said convex shell include different thicknesses of materials used to manufacture the shell.

19. The convex skin plate according to claim 17, further comprising at least two belt ears formed along at least two points on the outer edge of the convex shell, a positioning of said belt ears serving to control deformation of the convex shell.

20. The convex skin plate according to claim 19, wherein the belt ears are positioned farther away from the lateral axis than from the transition sections so as to prevent force from being applied within an area of the stoma during use.

* * * * *